US012682668B2

(12) United States Patent
Hahn et al.

(10) Patent No.: US 12,682,668 B2
(45) Date of Patent: Jul. 14, 2026

(54) DEVICE FOR PERFORMING MULTI-DETECTION ANALYSIS ON SAMPLE USING DEEP LEARNING-BASED DECODING OF ENCODED MAGNETIC PARTICLES, AND METHOD THEREFOR

(71) Applicant: KYUNGPOOK NATIONAL UNIVERSITY INDUSTRY-ACADEMIC COOPERATION FOUNDATION, Daegu (KR)

(72) Inventors: Young Ki Hahn, Seoul (KR); Moon-Chang Baek, Daegu (KR); Ho Young Jung, Daejeon (KR); Subin Park, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 265 days.

(21) Appl. No.: 18/294,591

(22) PCT Filed: Aug. 17, 2022

(86) PCT No.: PCT/KR2022/012223
§ 371 (c)(1),
(2) Date: Feb. 2, 2024

(87) PCT Pub. No.: WO2023/027408
PCT Pub. Date: Mar. 2, 2023

(65) Prior Publication Data
US 2024/0378909 A1 Nov. 14, 2024

(30) Foreign Application Priority Data
Aug. 23, 2021 (KR) ........................ 10-2021-0110739

(51) Int. Cl.
*G06V 20/69* (2022.01)
*G01N 33/543* (2006.01)
(Continued)

(52) U.S. Cl.
CPC ..... *G06V 20/698* (2022.01); *G01N 33/54326* (2013.01); *G06T 7/20* (2013.01);
(Continued)

(58) Field of Classification Search
None
See application file for complete search history.

(56) References Cited

U.S. PATENT DOCUMENTS

2013/0310280 A1 11/2013 Chee et al.
2015/0125873 A1* 5/2015 Newman .............. G01N 27/745
435/7.1
2021/0285909 A1 9/2021 Lee et al.

FOREIGN PATENT DOCUMENTS

KR 10-2013-0117145 A 10/2013
KR 20130117145 A * 10/2013 ............... G11B 5/00
(Continued)

OTHER PUBLICATIONS

Zhang et al., "Computational cytometer based on magnetically modulated coherent imaging and deep learning", Year: 2019, DOI: https://doi.org/10.1038/s41377-019-0203-5 (Year: 2019).*
(Continued)

*Primary Examiner* — Chan S Park
*Assistant Examiner* — Promotto Tajrian Islam
(74) *Attorney, Agent, or Firm* — Revolution IP, PLLC

(57) ABSTRACT

According to the present invention, a multi-detection analysis method of a biological sample includes a step of preparing a plurality of a magnetic encoded microparticles encoded in different types and introducing the plurality of a magnetic encoded microparticles into a sample of an analy-
(Continued)

sis target, a step of acquiring a video of the sample in a state where the sample is exposed to a rotating magnetic field, a step of inputting a time-series image included in the video into a pre-trained deep learning algorithm, analyzing rotation pattern characteristics of each magnetic encoded microparticle in the video over time through the deep learning algorithm, and classifying each magnetic encoded microparticle, and a step of multi-detecting a plurality of types of target materials in the sample based on a classification result of each magnetic encoded microparticle in the video.

4 Claims, 11 Drawing Sheets

(51) Int. Cl.
  *G06T 7/20* (2017.01)
  *G06V 10/82* (2022.01)
(52) U.S. Cl.
  CPC ............ *G06V 10/82* (2022.01); *G06V 20/693* (2022.01); *G06T 2207/10016* (2013.01); *G06T 2207/10056* (2013.01); *G06T 2207/10064* (2013.01); *G06T 2207/20081* (2013.01); *G06T 2207/20084* (2013.01); *G06T 2207/30024* (2013.01); *G06V 2201/03* (2022.01)

(56) References Cited

FOREIGN PATENT DOCUMENTS

| KR | 10-2019-0089636 | A | | 7/2019 | |
|----|-----------------|---|---|--------|---|
| KR | 20190089636 | A | * | 7/2019 | ........... G01N 33/531 |
| KR | 10-2020-0006695 | A | | 1/2020 | |

OTHER PUBLICATIONS

O'Conner et al., "Deep learning-based cell identification and disease diagnosis using spatio-temporal cellular dynamics in compact digital holographic microscopy", Year: 2020, DOI: 10.1364/BOE. 399020 (Year: 2020).*
Wenqiang Yan et al., "Machine Learning Approach to Enhance the Performance of MNP-Labeled Lateral Flow Immunoassay", Nano-Micro Letters, 2019-01, vol. 11 (1), p. 1-15, Article 7.
Yibo Zhang et al., "Computational cytometer based on magnetically modulated coherent imaging and deep learning", Light Science & Applications, Oct. 2019, 8:91.
International Search Report of PCT/KR2022/012223 mailed Nov. 23, 2022 from Korean Intellectual Property Office.
Kim, J. H. et al., "Multiplexed detection of pathogens using magnetic microparticles encoded by magnetic axes", Sensors and Actuators B: Chemical, 2019, vol. 285, pp. 11-16.

* cited by examiner

| video acquisition unit | decoding unit |
| detection unit | learning unit |
| output unit | control unit |

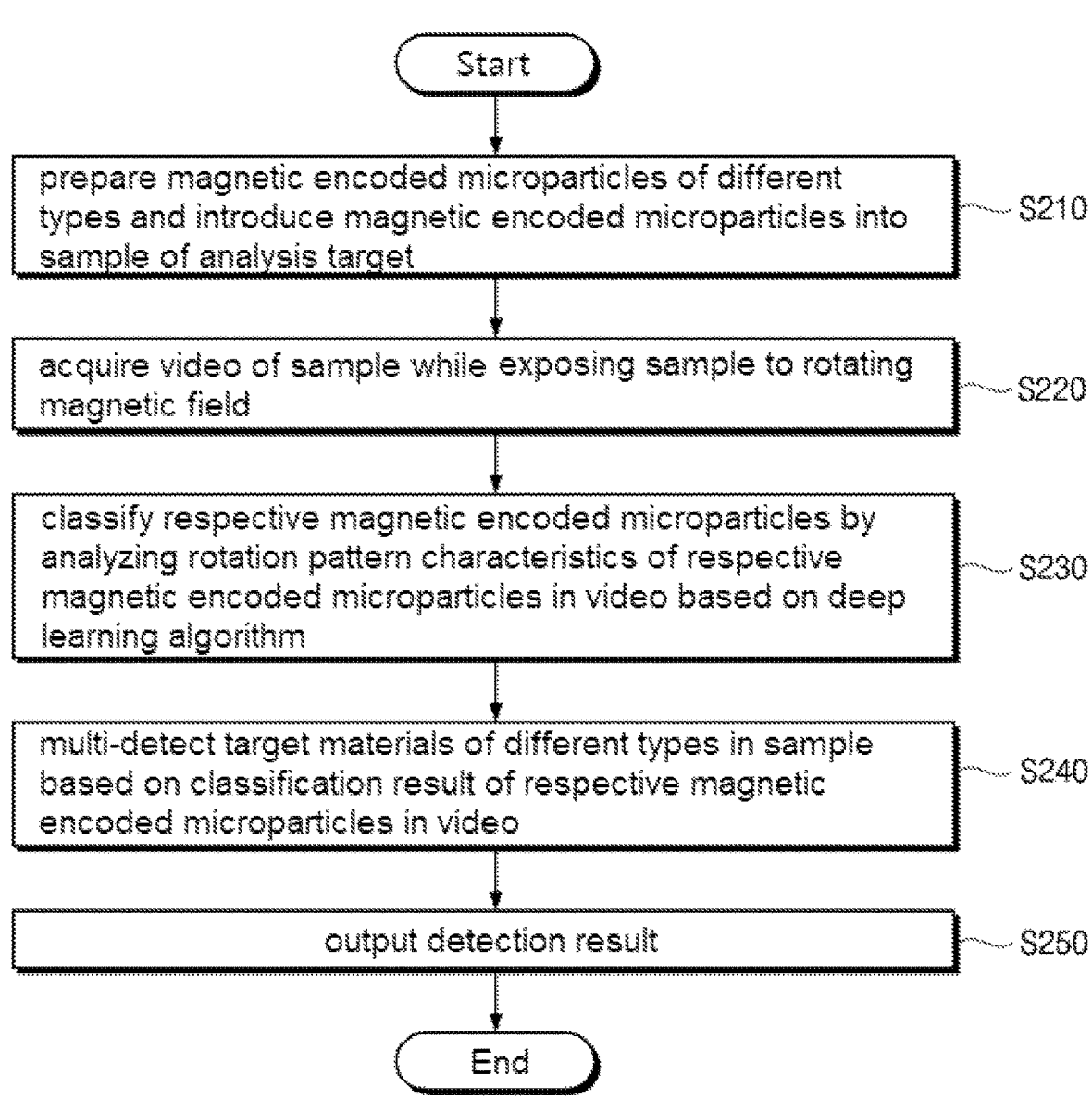

Start prepare magnetic encoded microparticles of different types and introduce magnetic encoded microparticles into sample of analysis target — S210 acquire video of sample while exposing sample to rotating magnetic field — S220 classify respective magnetic encoded microparticles by analyzing rotation pattern characteristics of respective magnetic encoded microparticles in video based on deep learning algorithm — S230 multi-detect target materials of different types in sample based on classification result of respective magnetic encoded microparticles in video — S240 output detection result — S250

End

Neodymium magnet

Acryl pannel

Straight magnetic field

| Diagonal axis (45°) | Horizontal axis (0°) | Vertical axis (90°) | Half pattern axis (90°&0°) |

FIG. 9

| exosome concentration (unit/mL) | 0 | $2.7 \times 10^7$ | $5.4 \times 10^7$ | $10.8 \times 10^7$ | $21.6 \times 10^7$ | $43.3 \times 10^7$ |
|---|---|---|---|---|---|---|
| PD-L1 | | | | | | |
| EpCAM | | | | | | |
| EGFR | | | | | | |

FIG. 10
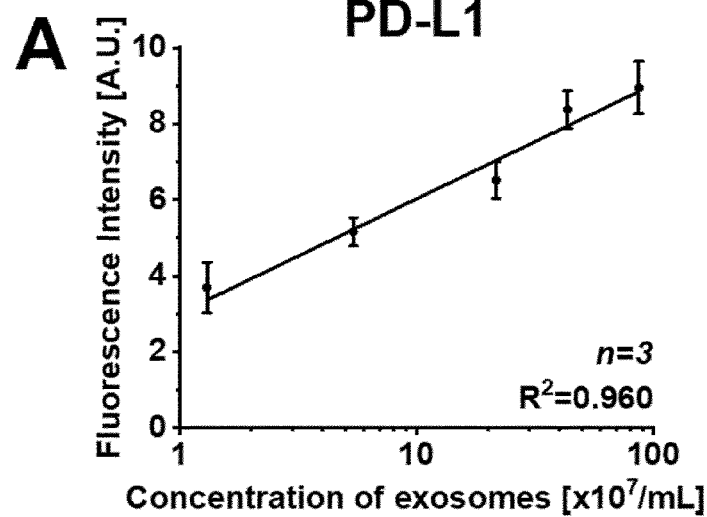
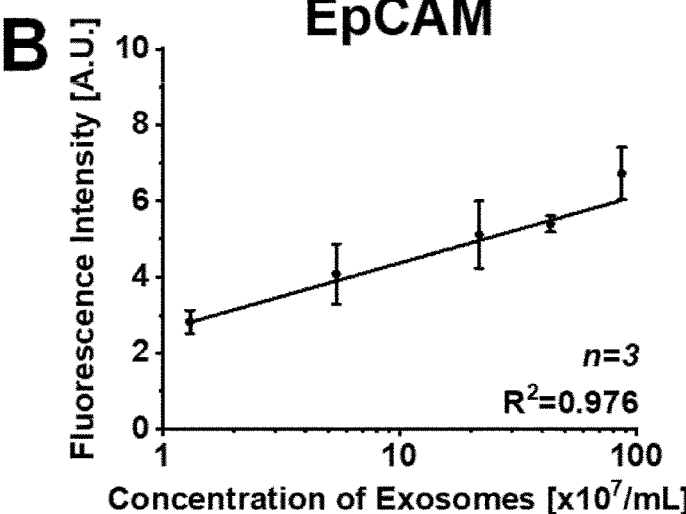
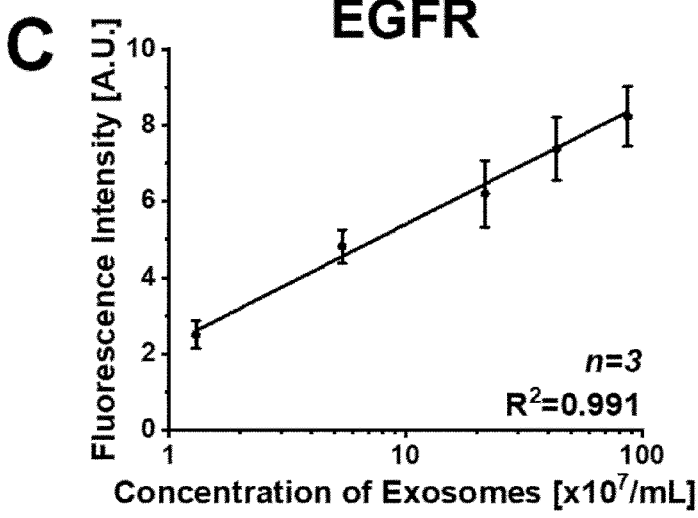

DEVICE FOR PERFORMING MULTI-DETECTION ANALYSIS ON SAMPLE USING DEEP LEARNING-BASED DECODING OF ENCODED MAGNETIC PARTICLES, AND METHOD THEREFOR

TECHNICAL FIELD

The present invention relates to a multi-detection analysis device and method of a sample using deep learning-based decoding of magnetic encoded microparticles, and more specifically, to a multi-detection analysis device and method that may quickly and accurately diagnose diseases from biological samples by using a magnetic force-based multi-detection diagnostic platform.

BACKGROUND ART

Exosomes are small vesicles with a size of 50 to 150 nm (nanometers) that are secreted from all cells and circulate throughout the body and participate in various physiological activities. The exosomes play an important role in intercellular communication and influence a significant number of cellular activities in human health and disease. The exosomes include proteins, nucleic acids, and lipids within membranes and cells thereof and contains abundant biomolecules from original cells. These properties induce different molecular pathways in exosomes and serve as potential biomarkers for early diagnosis of diseases.

In particular, cancer cells contain their own cancer metastasis-specific proteins into exosomes. In this case, the secreted exosomes include various elements related to cancer, and the exosomes are known to significantly contribute to cancer progression and metastasis in the relevant area by transferring the various elements related to cancer to normal cells and changing a tumor microenvironment favorably.

Due to the unique biological characteristics of exosomes, many studies are being conducted to utilize the exosomes specifically secreted from cancer cells as biomarkers in early diagnosis and prediction of cancer.

However, due to complexity of the human body and heterogeneity of tumors, it is obvious that a single biomarker alone may not accurately reflect a step of disease progression. Therefore, in order to achieve disease diagnosis with high accuracy and specificity, development of a platform for simultaneous detection of various biomarkers is required.

Recently, methods used for multiplexed detection of multiple target molecules may be broadly divided into a suspension array and a planar microarray. The suspension array has been further researched in recent years because the suspension array provides higher specificity and improved reproducibility compared to the planar microarray.

Many researchers have proposed methods using encoded particles as a diagnostic tool for simultaneously detecting multiple targets in a single sample. Different probe molecules are attached to different encoded particles and then react with a target sample to analyze a result, and in order to identify the attached probe molecule, each encoded particle has to be identifiable, and accordingly, each particle has to be encoded into a unique identifier.

Due to this, encoding methods based on various principles, such as spectroscopic, graphical, electronic, and physical methods, have been proposed, but the methods have disadvantages of requiring complex manufacturing processes and special optical equipment for decoding, despite excellent multi-detection capabilities thereof.

Therefore, there is a need to develop a new multi-detection diagnostic platform that applies a simpler encoding method and a decoding method that does not require complex devices.

The technology behind the present invention is disclosed in Korean Patent Publication No. 2019-0089636 (published on Jul. 31, 2019).

DISCLOSURE

Technical Problem

An object of the present invention is to provide a multi-detection analysis device and method that may quickly and accurately identify magnetic encoded microparticles of different types by using deep learning-based a rotation pattern discrimination technology and simultaneously detect different types of target materials in a biological sample in an image by using an identification result.

Technical Solution

According to the present invention, a multi-detection analysis method of a biological sample using a multi-detection analysis device using deep learning-based decoding includes a step of preparing a plurality of magnetic encoded microparticles encoded in different types and introducing the plurality of magnetic encoded microparticles into a sample of analysis targets, a step of acquiring a video of the sample in a state where the sample is exposed to a rotating magnetic field, a step of inputting time-series images included in the video into a pre-trained deep learning algorithm, analyzing rotation pattern characteristics of each magnetic encoded microparticle in the video over time through the deep learning algorithm, and classifying each magnetic encoded microparticle, and a step of multi-detecting a plurality of types of target materials in the sample based on a classification result of each magnetic encoded microparticle in the video.

Also, different capture antibodies for reacting with different types of target materials for each encoding type may be attached to the plurality of magnetic encoded microparticles, and the multi-detection analysis method may further include a step of sequentially introducing a detection antibody for detecting the target material and a fluorescent material attached to the detection antibody into the sample into which the plurality of magnetic encoded microparticles are introduced and reacting with each other.

Also, in the step of multi-detecting, an encoding type of each magnetic encoded microparticle may be identified in the video based on a classification result of each magnetic encoded microparticle in the video, intensity of the fluorescent material conjugated to the magnetic encoded microparticle may be analyzed for the identified each type, and concentration of a target material corresponding to a corresponding type may be quantified.

Also, the rotation pattern characteristics of the magnetic encoded microparticles may include at least one of a rotation speed and a rotation cycle of the magnetic encoded microparticle, whether there is a continuous rotation, whether an intermittent stop section occurs during rotation, an occurrence cycle of a stop section, and a time length of the stop section.

Also, the deep learning algorithm may be implemented by including a convolutional long-short-term memory network (Convolutional LSTM) for learning image analysis and time-variation information.

Also, the magnetic encoded microparticles may be photocured and manufactured to have a rod shape in a state where superparamagnetic nanoparticles mixed with a photocurable polymer material are aligned in a microchannel in a set direction according to an external magnetic field, and may be encoded in different types according to an alignment direction.

Also, an encoding type of the magnetic encoded microparticle may include a first type in which particles are aligned in a transverse direction (0°) that is a length direction of the rod, a second type in which particles are aligned in a longitudinal direction (90°), a third type in which particles are aligned in a diagonal direction (45°), a fourth type in which particles are aligned in a direction between 0° and 90°, excluding 45°, and a fifth type of a structure in which a plurality of nanoparticle blocks including particles aligned in different directions are arranged sequentially in the length direction.

In addition, the present invention provides a multi-detection analysis device for a biological sample, including a video acquisition unit configured to acquire an image of a sample of an analysis target in a state where a rotating magnetic field is applied to the sample prepared by introducing a plurality of magnetic encoded microparticles encoded in different types, a decoding unit configured to input a time-series image included in the video into a pre-trained deep learning algorithm, analyze rotation pattern characteristics of each magnetic encoded microparticle in the video over time through the deep learning algorithm, and classify each magnetic encoded microparticle, and a detection unit configured to multi-detect a plurality of types of target materials in the sample based on a classification result of each magnetic encoded microparticle in the video.

Also, a detection antibody for detecting the target material and a fluorescent material attached to the detection antibody may be sequentially introduced into the sample into which the plurality of magnetic encoded microparticles are introduced before the rotating magnetic field is applied, and react with each other.

Also, the detection unit may identify an encoding type of each magnetic encoded microparticle in the video based on a classification result of each magnetic encoded microparticle in the video, analyze intensity of the fluorescent material conjugated to the magnetic encoded microparticle for the identified each type, and quantify concentration of a target material corresponding to a corresponding type.

Advantageous Effects

According to the present invention, magnetic encoded microparticles encoded in different types are quickly and accurately identified by exposing different types of magnetic encoded microparticles to a rotating magnetic field and by performing deep learning analysis of a rotation pattern of each magnetic encoded microparticle with a video captured, and different types of target materials in a biological sample may be simultaneously detected from the video by using the identification result, and a quantitative analysis result may be provided by using the detection result.

The present invention may identify the type of each magnetic encoded microparticle detected from a video through a deep learning model, and thus, there is no need for a complex special optical apparatus to decode encrypted particles, sample analysis time may be reduced, disease-related exosomes may be quickly detected, and disease diagnosis time may be greatly shortened.

DESCRIPTION OF DRAWINGS

FIG. 1 is a diagram illustrating a configuration of a multi-detection analysis device for a biological sample, according to an embodiment of the present invention.

FIG. 2 is a diagram illustrating a multi-detection analysis method of a biological sample using FIG. 1.

FIG. 9 illustrates fluorescence intensity according to exosome concentration on magnetic encoded microparticles conjugated with different capture antibodies.

FIG. 10 illustrates diagrams of a relationship between concentration of exosomes reacted with magnetic encoded microparticles including different capture antibodies and the fluorescence intensity, according to an embodiment of the present invention.

BEST MODE

Figure 3:
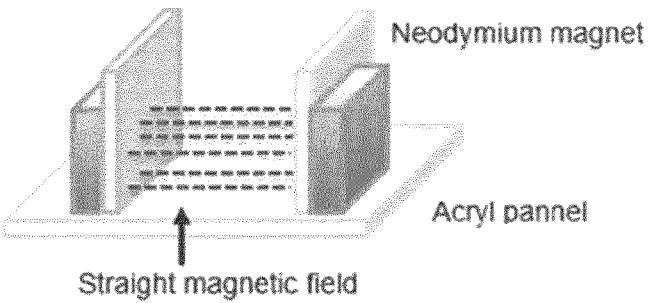
FIG. 3 illustrates a magnetic field device used to encode magnetic encoded microparticles, according to an embodiment of the present invention.

Then, embodiments of the present invention will be described in detail with reference to the accompanying drawings such that those skilled in the art to which the present invention belongs may easily practice the embodiments. However, the present invention may be implemented in many different forms and is not limited to the embodiments described herein. In addition, in order to clearly describe the present invention in the drawings, parts irrelevant to the description are omitted, and similar reference numerals are attached to similar parts throughout the specification.

Throughout the specification, when a portion or a unit is described to be "connected" to another portion or another unit, this includes not only a case of being "directly connected", but also a case of being "electrically connected" with other elements therebetween. In addition, "including" a certain component means that other components may be further included, rather than excluding other components unless otherwise stated.

The present invention relates to a multi-detection analysis device and method of a sample using deep learning-based decoding of magnetic encoded microparticles, and proposes a technology that may quickly and accurately identify different types of magnetic encoded microparticles in images by using a deep learning-based decoding technique and may perform simultaneous and multiple detection of different types of a target material in a biological sample by using an identification result.

In embodiments of the present invention, a sample of an analysis target may include blood, saliva, urine, and so on. A plurality of magnetic encoded microparticles encoded (encrypted) in different types are introduced into the sample of an analysis target. A rotating magnetic field is applied to a prepared sample so as to enable analysis of a rotation pattern of magnetic encoded microparticles (MEMP).

In an embodiment of the present invention, different capture antibodies for reacting with different types of target materials are respectively attached to a plurality of magnetic encoded microparticles for each encoding type. In addition, before applying a rotating magnetic field, a detection antibody for detecting a target material and a fluorescent material attached to the detection antibody may be sequentially introduced into a sample and reacted with each other.

In an embodiment of the present invention, magnetic encoded microparticles are manufactured to have a bar shape (bar-type) by being photo-cured in a state where superparamagnetic nanoparticles mixed with a photocurable polymer material are aligned in a microchannel in a set direction according to an external magnetic field.

Here, the magnetic encoded microparticles may be encoded into different types according to an alignment direction. For example, in addition to encoding in 0°, 45°, and 90° directions, a structure may be used in which a direction between 0° and 90° and multiple different directions are mixed together. The mixed structure includes a structure in which sections encoded in different directions with respect to a length direction of the magnetic encoded microparticle are sequentially arranged.

Figure 1:
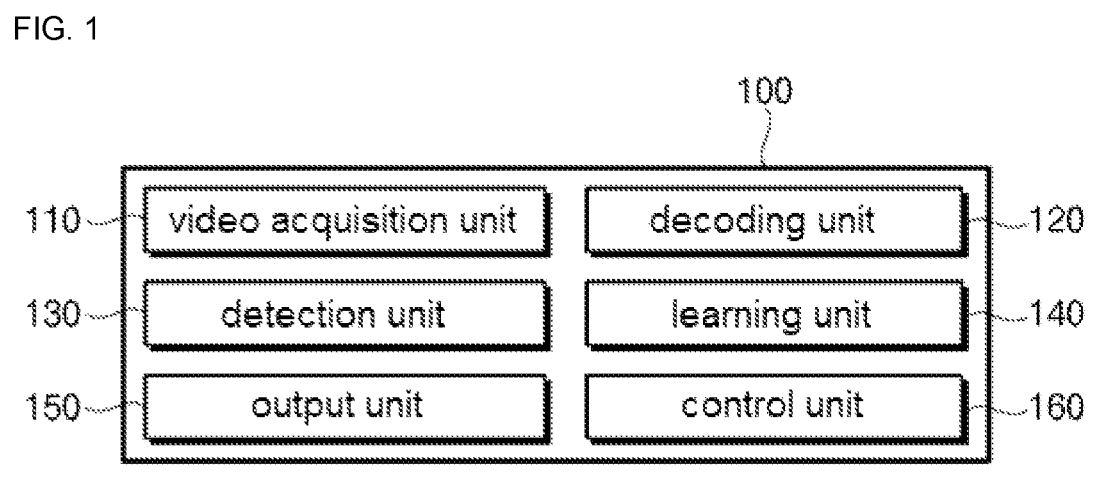

FIG. 1 is a diagram illustrating a configuration of a multi-detection analysis device for a biological sample, according to an embodiment of the present invention.

As illustrated in FIG. 1, a multi-detection analysis device 100 for a biological sample, according to an embodiment of the present invention, includes a video acquisition unit 110, a decoding unit 120, a detection unit 130, a learning unit 140, an output unit 150, and a control unit 160.

First, the video acquisition unit 110 acquires a video of a sample in a state where a rotating magnetic field is applied to the sample of an analysis target prepared by inserting different types of magnetic encoded microparticles. In this case, the video may correspond to a video captured during a set time (for example, 10 seconds or 1 minute).

The video acquisition unit 110 may collect videos obtained by capturing a sample from an image capturing device. Here, the image capturing device may include at least one of a camera (for example, a CCD camera) and a microscope.

The video acquisition unit 110 may receive a video by being connected to the image capturing device through a wired or wireless network. Also, the video acquisition unit 110 may include the image capturing device.

The video acquisition unit 110 may acquire a video obtained by capturing a sample from the image capturing device and transmit the video to the decoding unit 120. A video consists of images of multiple frames, and for example, the video may include images of multiple frames per second (for example, 30 frames).

The decoding unit 120 inputs time-series images included in the video into a previously trained deep learning algorithm, analyzes rotation pattern characteristics of each magnetic encoded microparticle in the video over time through the deep learning algorithm, and classifies each magnetic encoded microparticle.

The decoding unit 120 receives a video of a set time length (for example, 10 seconds or 1 minute) from the video acquisition unit 110 and decodes each magnetic encoded microparticle in the video by applying images of multiple frames constituting a unit video to a pre-trained deep learning-based classification model. Here, the deep learning-based decoding means identifying the types of magnetic encoded microparticles that were previously encoded into different types through deep learning analysis of a video.

In this way, according to the embodiment of the present invention, the rotation pattern characteristics of each magnetic encoded microparticle included in a video over time are analyzed by a pre-trained deep learning-based classification model, and accordingly, different types of magnetic encoded microparticles in the video may be distinguished.

Here, the rotation pattern characteristics of the magnetic encoded microparticle may include at least one of a rotation speed and a rotation cycle of the magnetic encoded microparticle, whether there is a continuous rotation, whether there is an intermittent stop section during rotation, an occurrence period of the stop section, and a time length of the stop section. The rotation pattern characteristics of magnetic encoded microparticles may appear uniquely for each encoding type.

Depending on encoding types, the magnetic encoded microparticles may rotate continuously without stopping according to time but may have a periodically stopping pattern during rotation. In addition, depending on encoding types, the rotation speed or period of the magnetic encoded microparticle, whether there is a stop section, the time length of the stop section, and so on may be changed.

According to the embodiment of the present invention, a deep learning algorithm may include a convolutional long-short-term memory (LSTM) (hereinafter referred to as ConvLSTM) neural network for learning image analysis and time variation information.

The ConvLSTM neural network may decode (classify) each magnetic encoded microparticle by analyzing the rotation pattern characteristics of the magnetic encoded microparticles from an input image.

The decoding unit 120 may provide a result of classifying each magnetic encoded microparticle in a video to the detection unit 130. Here, the decoding unit 120 provides a classification result for each object in an image and may map the classification result to an object position and provide a mapping result.

The deep learning algorithm may be pre-trained by the learning unit 140. For each encoding type, the learning unit 140 learns a rotation pattern of the magnetic encoded microparticles by using a video taken by exposing a rotating magnetic field to the magnetic encoded microparticles. When learning is completed, the type (encoding type) of each magnetic encoded microparticle in a video may be classified from an input image.

For example, the learning unit 140 may receive a time-specific image of a training video in which the encoding type is labeled for each object in the image and learns the rotation pattern characteristics of each object in the image and may be trained to classify the type (encoding type) of each object in the video by learning the rotation pattern characteristics of each object in the video. That is, the deep learning algorithm may receive an image with a corresponding encoding type labeled for each magnetic encoded microparticle in the image and learn the rotation pattern characteristics of the magnetic encoded microparticle for each type.

In this way, the learning unit 140 may analyze a video taken by exposing a rotating magnetic field to the magnetic encoded microparticles through a deep learning algorithm and pre-learns the rotation pattern characteristics of the magnetic encoded microparticles for each different encoding type, thereby constructing deep learning-based classification model. The learning unit 140 may implement a classification model of a convolutional LSTM structure.

Here, the learning unit 140 and the decoding unit 120 may be included or built in a decoding processor. The decoding processor may be equipped with an artificial intelligence-based classification model, provide relevant detection results, and update and renew a classification model.

The detection unit 130 detects multiple different types of target materials in a biological sample based on the classification result of each magnetic encoded microparticle in a video and provides a detection result.

In this case, the detection result may include a video taken by capturing a biological sample, whether a target material is detected in the video, the type and number of detected target materials, a quantification result of the target material, and so on.

For example, when observing four magnetic encoded microparticles encoded in different types in a state where the four magnetic encoded microparticles are inserted into a sample and a rotating magnetic field is applied to the four magnetic encoded microparticles, maximum four types of target materials may be detected from the sample. Here, the target material may correspond to exosomes related to disease.

A principle of detection of a target material is briefly described as follows. As described above, different types of capture antibodies are attached (conjugated) to each of the magnetic encoded microparticles encoded in different types.

Each type of magnetic encoded microparticles to which different capture antibodies are attached is introduced into a sample, and then magnetic encoded microparticles react with a target material (exosome) included in the sample for a set period of time, and accordingly, a magnetic encoded microparticle-exosome reaction product is generated in the sample. In this case, different capture antibodies attached to each type of magnetic encoded microparticles operate to react with different specific target materials (exosomes).

Thereafter, when a detection antibody is introduced into the sample, the exosome, which is a target material, combines with the detection antibody, and thereby, a magnetic encoded microparticle-exosome-detection antibody reaction product is generated. In addition, when a fluorescent material is introduced into the sample, the detection antibody reacts with the fluorescent material, and the fluorescent material is attached.

Here, in addition to the method of introducing a detection antibody and a fluorescent material sequentially to react with each other as described above, it is also possible to introduce a material in which the detection antibody is combined with the fluorescent material at once and react with each other.

When the magnetic encoded microparticles in which final reaction is completed are exposed to an external rotating magnetic field, the magnetic encoded microparticles rotate in a unique rotation pattern corresponding to an encoding type of the magnetic encoded microparticles.

The decoding unit 120 decodes each magnetic encoded microparticle inserted into a biological sample by analyzing a rotation pattern characteristics of each magnetic encoded microparticle in a video and classifies the encoding type.

The detection unit 130 identifies the encoding type of each magnetic encoded microparticles in the video based on the classification result of each magnetic encoded microparticle in the video received from the decoding unit 120, and analyzes the intensity of a fluorescent material combined with the magnetic encoded microparticle for each identified type, and quantifies concentration of the target material corresponding to the corresponding type.

The detection unit 130 may detect the intensity of light emitted from a fluorescent material in a video and extract the concentration of a target material.

To this end, the detection unit 130 may extract or calculate a concentration value corresponding to the intensity of the currently detected light by using a function that defines the concentration of the target material corresponding thereto for each intensity of light or an information table. Here, the function or information table may be constructed for each target material. In this case, the information table may have a graph form defining a relationship between fluorescence intensity and concentration in addition to a general table form.

In this way, the detection unit 130 may quantitatively analyze the concentration of a target material by detecting and using the fluorescence intensity emitted from each magnetic encoded microparticle in a video. Here, when the fluorescence intensity of a specific magnetic encoded microparticle is 0, this means that a specific target material corresponding thereto does not exist in a sample.

In this way, when the fluorescence intensity of each magnetic encoded microparticle encoded in each type is known, presence or absence of detection and detection concentration in a sample may be checked for each target material corresponding to each type.

The detection unit 130 may analyze the fluorescence intensity from the video obtained by an image capturing device. For example, the fluorescence intensity of each magnetic encoded microparticle in a video may be acquired by using a microscope equipped with a CCD camera. Various known techniques and devices may also be used to analyze the fluorescence intensity of magnetic encoded microparticles.

The control unit 160 controls operations of the respective units 110 to 140 and data flow between the respective units. In addition, the control unit 160 may include a built-in pre-programmed processor required for various controls, operations, and data processing.

This control unit 160 may store input/output data of a device, data processing results, and so on in memory. For example, the control unit 160 may match a video taken by capturing a biological sample, images of respective frames, whether at least one target material is detected, a quantitative analysis result of a target material, and so on to an identification number of the sample and store the matched data and may output the related content through the output unit 150.

The multi-detection analysis device 100 of the present invention may be implemented as an online or offline platform of a web server or app server that detects a target material in a sample by receiving a video taken by capturing a sample into which multiple types of magnetic encoded microparticles are introduced and by performing deep learning analysis and provides a detection result, or may be implemented in the form of an application program, an application, or so on in a user terminal or so on.

Also, the multi-detection analysis device 100 may be implemented in the form of a user terminal, such as a computer, and the computer may include a processor, memory, a user interface input/output device, a storage device, and so on.

The present invention comprehensively provides the type of a target material in a biological sample, a quantification result of the target material, and so on by using deep learning-based decoding of magnetic encoded microparticles of different types that react with different types of antigens (target materials) in the sample.

In addition, the present invention may quickly and accurately diagnose various diseases from a small amount of biological samples. That is, various diseases or disease factors may be diagnosed quickly and easily by simply monitoring and analyzing a video taken for a set period of time by introducing different types of magnetic encoded microparticles into a biological sample and exposing the magnetic encoded microparticles to a rotating magnetic field.

Next, based on the above-described configuration, a multi-detection analysis method of a biological sample is described in detail.

FIG. 2 is a diagram illustrating a multi-detection analysis method of a biological sample using FIG. 1.

First, a plurality of magnetic encoded microparticles encoded in different types are prepared and introduced into a biological sample of an analysis target (for example, blood, saliva, urine, or so on) (S210).

Figure 4:
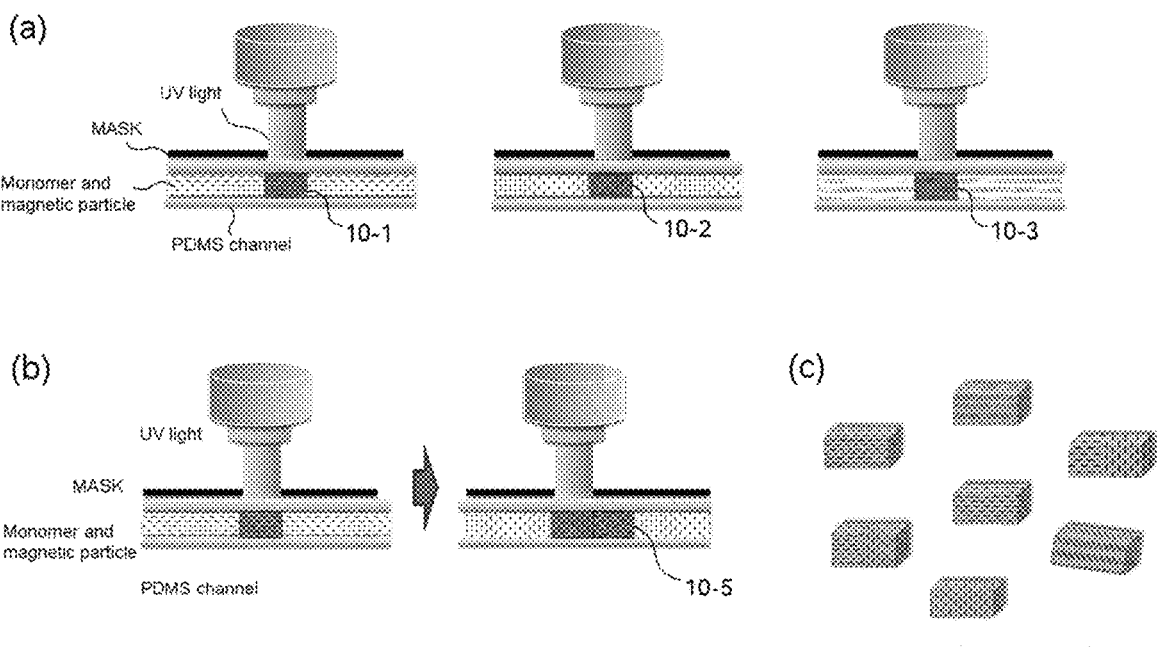
FIG. 4 illustrates a principle of photo-curing and manufacturing magnetic encoded microparticles, according to an embodiment of the present invention.

FIG. 3 illustrates a magnetic field device of an embodiment of the present invention which is used for encoding magnetic encoded microparticles, and FIG. 4 illustrates a principle of photo-curing and manufacturing the magnetic encoded microparticles according to an embodiment of the present invention.

A top picture of FIG. 3 illustrates a magnetic field generating device. When a magnetic encoded microparticle is encoded, a static magnetic field is used. Due to this, the magnetic field generating device operates to generate a static magnetic field. FIG. 3 illustrates that the static magnetic field is generated through magnets mounted on both ends. Also, the magnetic field generating device may also operate to generate a rotating magnetic field of which magnetic field direction changes with time.

As illustrated in bottom pictures of FIG. 3, magnetic encoded microparticles may be encoded into different types according to an axial direction of the static magnetic field. Here, the magnetic encoded microparticles each have a bar shape and may be manufactured to have the same length.

Here, an encoding type of the magnetic encoded microparticles may include a first type in which particles are aligned in a transverse direction (0°) which is a length direction of a rod, a second type in which particles are aligned in the longitudinal direction (90°), a third type in which particles are aligned in a diagonal direction (45°), a fourth type in which particles are aligned in directions between 0° and 90° excluding 45°, and a fifth type in which at least two of the first type to the fourth type are combined with each other. In this case, the fifth type has a structure in which a plurality of nanoparticle blocks including particles aligned in different directions are arranged sequentially in the length direction.

In an embodiment of the present invention, the magnetic encoded microparticles may be manufactured within a microchannel (PDMS channel). For example, the magnetic encoded microparticles may be manufactured by injecting a mixed solution of a polymer material and superparamagnetic nanoparticles (SMNP) into a microchannel, exposing the mixed solution to a static magnetic field to align the super-paramagnetic nanoparticles in a direction of a magnetic field, and by UV-curing a target area.

That is, the superparamagnetic nanoparticles may form a mixture of a polymer material, a curing agent, and so on, may be exposed to an external static magnetic field, may be aligned in a chain shape according to the direction of the magnetic field, and then may be manufactured by polymer polymerization using a method such as photo curing. In this case, by changing the direction of the external static magnetic field, the superparamagnetic nanoparticles may be aligned at various angles, and chain directions corresponding to the magnetic field direction may be respectively formed.

The used polymer material is a material that may be cured and form microparticles and may be any one of poly-(ethylene glycol) diacrylate, polystyrene, polymethyl-methacrylate (PMMA), silica, polyvinyltoluene (PVT), styrene/butadiene (S/B), copolymer, and styrene/vinyltoluene (S/VT).

An encoding process of magnetic encoded microparticles is described in more detail as follows.

First, a mixed solution of a polymer monomer and super-paramagnetic nanoparticles is injected into a microchannel, and the superparamagnetic nanoparticles in the mixed solution are aligned according to an axial direction of a magnetic field applied from the outside through a magnetic field generating device.

(a) of FIG. 4 illustrates a state in which superparamagnetic nanoparticles in a mixed solution are aligned in different directions by an external magnetic field.

Next, as illustrated in (a) of FIG. 4, a mask having an open surface is placed on a target area of the mixed solution in the microchannel (PDMS channel), and then UV light is emitted through the open surface of the mask to UV-cures the target area. Thereafter, when a UV-cured block portion is separated from the microchannel, the magnetic encoded microparticles (MEMP) encoded in set directions (for example, 0°, 90°, and 45° directions) are manufactured.

(a) of FIG. 4 illustrates a state in which UV-curing is performed by applying a mask to some surfaces of the mixed solution aligned in different directions by using static magnetic fields in different axial directions. Therethrough, first, second, and third types of magnetic encoded microparticles 10-1, 10-2, and 10-3 respectively aligned in 0°, 90°, and 45° directions are manufactured. The first type has a horizontal pattern, the second type has a vertical pattern, and the third type has a diagonal pattern. Also, a nanoparticle of the fourth type corresponds to a magnetic encoded microparticle encoded in a single direction, thereby being manufactured according to the same principle described above.

(b) of FIG. 4 illustrates a principle of manufacturing a magnetic encoded microparticle of the fifth type. As illustrated in (b) of FIG. 4, a magnetic encoded microparticle 10-5 of the fifth type has a structure in which a plurality of nanoparticle blocks with particles aligned in different directions are sequentially arranged in a length direction. The magnetic encoded microparticle 10-5 of the fifth type corresponds to a magnetic encoded microparticle encoded in multiple directions.

(c) of FIG. 4 illustrates states of rod-shaped magnetic encoded microparticles manufactured in various types. In this way, according to the present invention, various types of magnetic encoded microparticles may be encoded and manufactured.

Next, a method of encoding magnetic encoded microparticles of a fifth type having a mixed pattern is described with reference to (b) of FIG. 4. (b) of FIG. 4 illustrates a method of manufacturing magnetic encoded microparticles having a mixed structure of the first type (0°) and the second type (90° direction).

First, in a state where the mixed solution is injected into the microchannel, an external magnetic field is applied in the first direction to align the superparamagnetic nanoparticles in the mixed solution in the first direction, and then a mask is placed on a first target area of the mixed solution and UV-curing is performed to form a first nanoparticle block (a left picture of (b) of FIG. 4).

Here, a direction in which a magnetic field is applied may be adjusted by changing an arrangement of the microchannel for a magnetic field generating device, and the magnetic field generating device may directly change the direction in which the magnetic field is applied.

Next, an external magnetic field is applied in the second direction to align the superparamagnetic nanoparticles in the mixed solution in the second direction, and then a mask is placed on a second target area adjacent to the first target area and UV-curing is performed to form a second nanoparticle block. According to this, the second nanoparticle block is cured next to the cured first nanoparticle block, and thereby, a joined structure is made.

Thereafter, the entire UV-cured block portion is separated from the microchannel, and the magnetic encoded microparticle 10-5 encoded in multiple directions is manufactured. In this way, the magnetic encoded microparticle of the fifth type has a structure in which at least two nanoparticle blocks (at least two different patterns) including particles aligned in different directions are sequentially arranged in a length direction.

The fifth type has a structure in which N patterns (N is 2 or more) are connected to each other in series, and an opening of a mask used during manufacturing may have a diameter of a size of 1/N compared to an opening of a mask used for the first type. Therethrough, manufacturing lengths of the magnetic encoded microparticles may be equal to each other.

Figure 5:
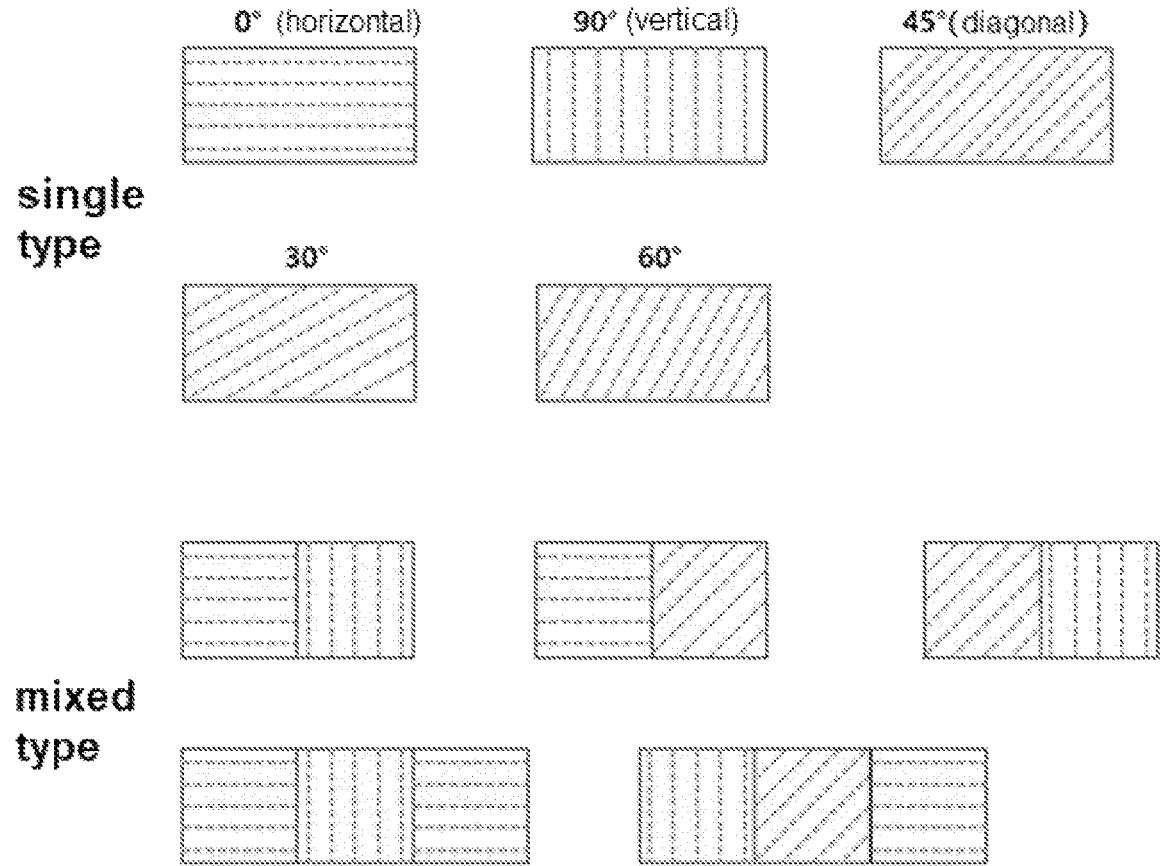
FIG. 5 illustrates various encoding types according to an embodiment of the present invention.

FIG. 5 illustrates various encoding types according to an embodiment of the present invention. In FIG. 5, not only the first to fourth types of magnetic encoded microparticles aligned in 0°, 90°, 45°, 30°, and 60° directions, but also the fifth type of mixed magnetic encoded microparticles composed of a combination thereof may be seen.

Meanwhile, in the embodiment of the present invention, each of the magnetic encoded microparticles encoded in different types is introduced into a sample in a state of being conjugated with different types of capture antibodies.

The capture antibody immobilized on a magnetic encoded microparticle for detecting exosome includes at least one of Anti-PD-L1 (Anti-Programmed Death-Ligand 1), Anti-EpCAM (Anti-Epithelial cell adhesion molecule), and Anti-EGFR (Anti-Epidermal growth factor receptor). Also, the capture antibody is not limited thereto and may include various other antibodies.

Also, a detection antibody may include at least one of Anti-CD63-Biotin, Anti-CD81-Biotin, and Anti-CD9-Biotin, or a mixture of three antibodies. Also, the detection antibody is not limited thereto and may include various other antibodies.

Here, the magnetic encoded microparticle to which the capture antibody is attached reacts with a specific target material (exosome) included in a sample.

In this case, for conjugating through specific reactions between biomaterials, at least one of exosome surface protein-antibody reaction, antigen-antibody reaction, Avidin or NeutrAvidin or StreptAvidin-Biotin reaction, and a reaction between complementary DNA, Immunoglobulin G-Protein A, Protein G, Protein A/G, and Protein L may be performed on a surface of the magnetic encoded microparticle.

According to the reaction, a magnetic encoded microparticle-exosome reaction product is generated in the sample. Also, different capture antibodies attached to each type of magnetic encoded microparticles react with different specific target materials (exosomes).

A target material to be detected in the embodiment of the present invention may be an exosome derived from a cell. Here, the cell from which exosome is derived may include at least one of normal embryonic kidney cell line (HEK293T), human breast cancer cell lines (MDA-MB231, MCF7), human colon cancer cell line (HCT 116), and human melanoma cell line (SK-MEL-28). Also, the cell from which the exosome is derived is not limited thereto and may include various other cells.

Here, after step S210 in which the magnetic encoded microparticle is introduced into a sample, a step of sequentially introducing a detection antibody and a fluorescent material into the sample to react is performed. Step S220 is performed in which, when all of the reactions are completed, the sample is exposed to a rotating magnetic field and observed is performed.

Specifically, after step S210, the detection antibody is introduced into the sample and reacted. According to this when exosome, which is a target material, combines with a detection antibody, a magnetic encoded microparticle-exosome-detection antibody reaction product is generated.

Next, a fluorescent material is introduced into a sample and reacted. According to this, the detection antibody reacts with the fluorescent material, and the fluorescent material is attached thereto. As a result, the fluorescent material is conjugated with the magnetic encoded microparticle. In this case, the fluorescent material may correspond to streptavidin to which the fluorescent material is attached. That is, StreptAvidin-FITC, which may conjugate with detection antibody-biotin, may be used as a fluorescent material for quantitative analysis of exosome.

Thereafter, the video acquisition unit 110 acquires a video of the sample in a state where a final reaction is completed and the prepared sample is exposed to a rotating magnetic field (S220). For example, a plate containing a sample is placed on a magnetic field generating device that provides a rotating magnetic field, and a video of the sample is taken and acquired in a state where a rotating magnetic field of a set intensity condition is applied.

When the magnetic encoded microparticle in which the final reaction is completed is exposed to a rotating magnetic field, the magnetic encoded microparticle rotates with a unique rotation pattern corresponding to an encoding type, and by analyzing the rotation pattern, an encoding type of each magnetic encoded microparticle may be determined. The video acquisition unit 110 transmits the acquired video to the decoding unit 120.

The decoding unit 120 decodes each magnetic encoded microparticle by analyzing rotation pattern characteristics of each magnetic encoded microparticle in a video based on a deep learning algorithm (S230).

Specifically, time-series images included in a captured video are input to a pre-trained deep learning algorithm, and the rotation pattern characteristics of each magnetic encoded microparticle in the video over time are analyzed by the deep learning algorithm, and thereby, respective magnetic encoded microparticles are classified. The decoding unit 120 transmits a decoding result to the detection unit 130.

In the embodiment of the present invention, a deep learning model implemented with a ConvLSTM neural network is used. The ConvLSTM neural network may decode each magnetic encoded microparticle by using the rotation pattern characteristics of each magnetic encoded microparticle analyzed from input time-series images.

Next, the detection unit 130 performs multi-detection of a plurality of types of target materials in a sample based on a classification result of respective magnetic encoded microparticles in the video (S240).

In this case, the detection unit 130 identifies encoding types of respective magnetic encoded microparticles in the video from the decoding result, analyzes intensity of a fluorescent material conjugated with the respective magnetic encoded microparticles for each identification type, and analyzes concentration of a target material corresponding to a relevant type. In this case, a relationship table between the concentration and the intensity of the fluorescent material, a function, a graph, and so on may be used.

The output unit 150 may output a captured video of a biological sample, images of respective frames constituting the video, whether a target material is detected from the biological sample, the type of detection, a quantitative analysis result of the target material, and so on through a display, a network-connected user terminal, or so on. Here, the user terminal may include a desktop computer, a tablet PC, a smartphone, a smart pad, a laptop computer, and so on.

The embodiment of the present invention provides a multi-exosome detection method, and the multi-exosome detection method includes a step of reacting a capture antibody immobilized on an magnetic encoded micropar-ticle with each exosome, a step of introducing a biotinylated detection antibody into a sample and reacting therewith to conjugate with an magnetic encoded microparticle-exosome reaction, a step of introducing streptavidin to which a fluorescent material is attached into a sample to react with biotin on an magnetic encoded microparticle-exosome-de-tection antibody reaction, a step of acquiring a rotation video by exposing the magnetic encoded microparticle in which a final reaction is completed to an external rotating magnetic field and analyzing and decoding a rotation pattern by using a deep learning algorithm, and a step of quantitatively analyzing concentration of exosome by detecting intensity of a fluorescent material conjugated with the magnetic encoded microparticle.

Figure 6:
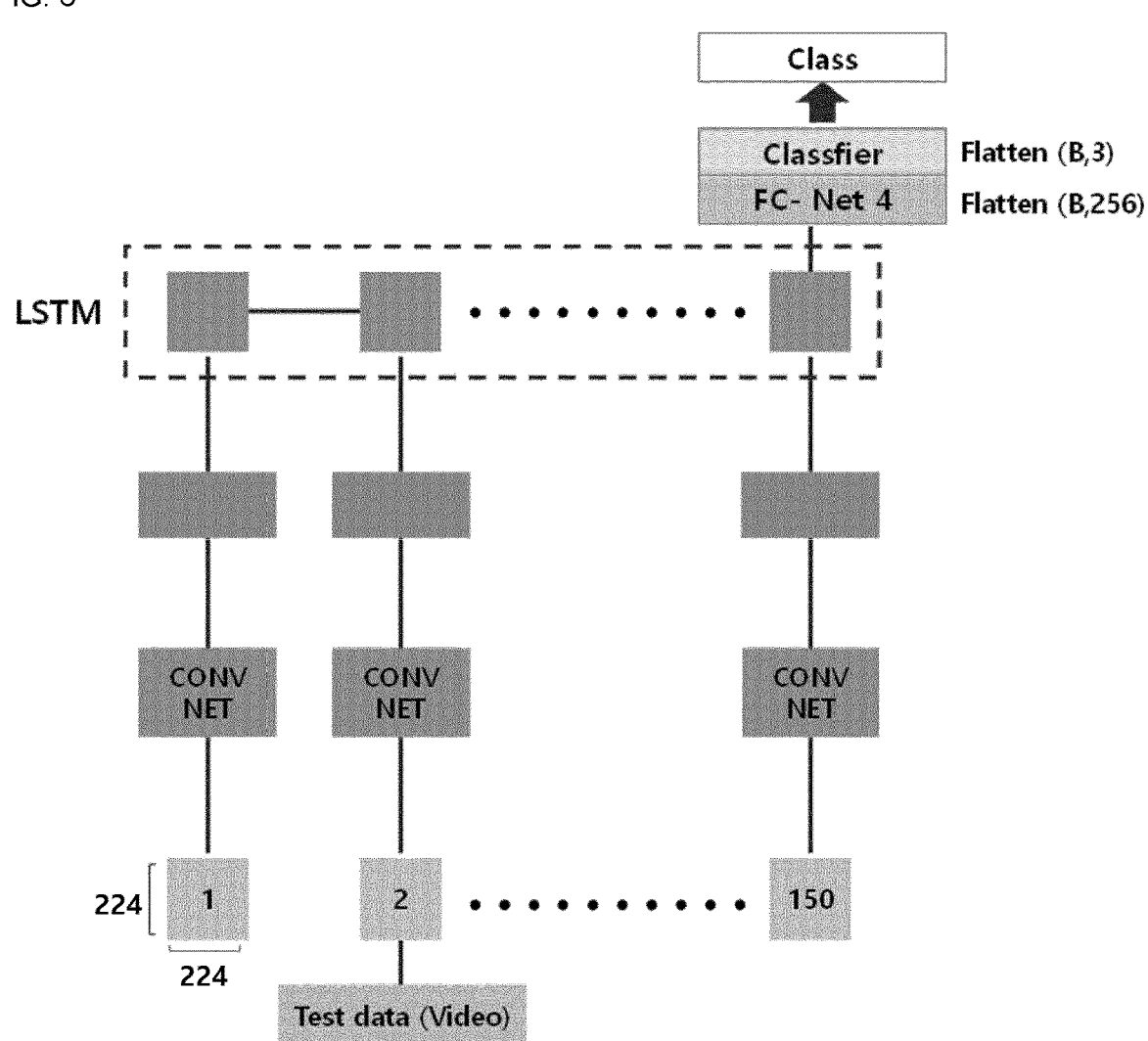
FIG. 6 illustrates a structure of a time-series analysis deep learning model of convolutional features, according to an embodiment of the present invention.

FIG. 6 is a diagram illustrating a structure of a time-series analysis deep learning model of convolutional features according to an embodiment of the present invention. FIG. 6 illustrates a deep learning-based magnetic encoded microparticle classification model and illustrates a structure in which magnetic encoded microparticle feature extraction based on a convolutional neural network is combined with time-series analysis based on a long-term memory neural network (LSTM neural network).

In the embodiment of the present invention, a length of a unit video used for learning a neural network is 5 seconds, and a total of 150 images obtained by sampling the 5-second video at 30 frames per second were input to a ConvLSTM neural network for learning. In this case, an original image having a size of H 760×W 1200 was adjusted to a size of H 244×W 244 and applied to neural network learning. A specific embodiment of the present invention is described below.

<Example 1> Chip Manufacturing for Magnetic Encoded Microparticle

A microfluidic device for manufacturing microparticles encoded by alignment of superparamagnetic nanoparticles was manufactured through a Poly(dimethylsiloxane) (PDMS) molding process.

PDMS and a curing agent were mixed at a ratio of 10:1, placed on a wafer mold patterned with SU-8 photoresist, and cured by heating at 80° C. for 40 minutes. A PDMS device including a microfluidic channel was removed and bonded to a cover glass covered with a layer of PDMS through oxygen plasma treatment.

<Example 2> Manufacture of Magnetic Encoded Microparticles

Under an external static magnetic field, superparamag-netic nanoparticles may be aligned to form a chain-like structure along a magnetic field. By using this phenomenon, microparticles encoded with superparamagnetic nanopar-ticle chains aligned in multiple directions were manufac-tured.

Figure 7:
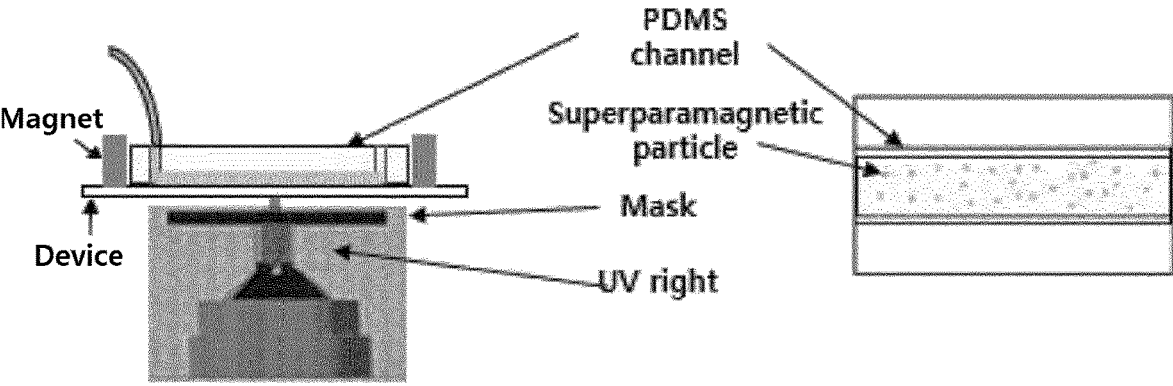
FIG. 7 is a view illustrating a process of manufacturing magnetic encoded microparticles, according to an embodiment of the present invention.

FIG. 7 is a view illustrating a process of manufacturing magnetic encoded microparticles, according to an embodi-ment of the present invention.

First, a photo mask is aligned and attached to the bottom of a PDMS microchannel, a mixed solution of a monomer and superparamagnetic nanoparticles is filled in the micro-channel, and then the microchannel is exposed to an external magnetic field. The microchannel may be set in a device that generates a parallel magnetic field.

In this case, the device may be manufactured to have a penetrated central portion such that UV light may pass therethrough. Also, when the device is formed of a trans-parent material, a separate through-hole may be omitted.

In order to form an external magnetic field, neodymium magnets were placed on both sides of a magnetic field generating device as illustrated in FIGS. 3 and 7 to generate a parallel magnetic field between both magnets. Here, by changing an installation direction of the microchannel for the magnetic field generating device, magnetic encoded microparticles encoded in different types may be manufac-tured.

A UV light source may be used as an optical apparatus for photopolymerization of a UV-curable polymer, and an opti-cal apparatus consisting of an objective lens was set up. When the superparamagnetic nanoparticles are aligned in the microchannel and exposed to UV light, a monomer solution including the superparamagnetic nanoparticles is polymerized by the UV light in 1 second by the UV light transmitted through a photomask.

According to the present invention, it is possible to generate magnetic encoded microparticles with chains in each direction, and in the embodiment of the present inven-tion, magnetic encoded microparticles encoded in three directions including horizontal (0°), diagonal (45°), and vertical (90°) directions were manufactured. The manufac-tured magnetic encoded microparticles each have a rod shape and a size of 300 μm×100 μm×100 μm.

<Example 3> Method of Immobilizing Magnetic Encoded Microparticle and Exosome Capture Antibody In order to conjugate an antibody to a magnetic encoded microparticle (MEMP), a photoimmobilization process was applied by using Bz (benzylamine hydrochloride) as a linker. Biotin and fluorescence-labeled Streptavidin were used to check a linker function of Bz. Bz (100 μg/ml) and Biotin (100 μg/ml) were mixed, and 100 μl of a mixed solution was added together with magnetic encoded microparticles and reacted. During reaction, a UV light (λ=365 nm) was emitted for 20 minutes at intensity of 18 mW/cm². After the reaction, the magnetic encoded microparticles were washed, and the magnetic encoded microparticles were incubated in a PBS solution including 5% bovine serum albumin (BSA) for 1 hour to block excess activated Bz, and then, the magnetic encoded microparticles were washed with PBS.

The magnetic encoded microparticles were reacted with fluorescence-labeled Streptavidin (100 μg/ml) at room temperature for 30 minutes and washed with PBS. A fluorescence image of the conjugated biotin and fluorescence-labeled Streptavidin was checked by using a fluorescence microscope equipped with a CCD. For exosome multi-analysis, capture antibodies was conjugated with magnetic encoded microparticles by applying a photocuring process. A capture antibody of 20 μg/ml (in PBS) and Bz of 500 μg/ml (in PBS) were used, and the capture antibody, a Bz solution, and respective magnetic encoded microparticles were mixed together, exposed to UV light for 20 minutes, and then washed with PBS. After completing a reaction, the magnetic encoded microparticles were stored in PBS at 4° C.

<Example 4> Cell Preparation for Exosome Extraction and Exosome Extraction

Five cell lines including normal embryonic kidney cell line (HEK293T), human breast cancer cell lines (MDA-MB231, MCF7), human colon cancer cell line (HCT 116), and human melanoma cell line (SK-MEL-28) were used and exosomes were extracted.

HEK293T, MCF7, and MDA-MB231 cells were cultured in high-glucose Dulbecco's Modified Eagle's Medium, SK-MEL-28 cells were cultured in Minimum Essential Medium, and HCT116 cells were cultured in RPMI 1640 medium. All culture media include 10% fetal bovine serum (FBS, Hyclone) and 1% antibiotics (Hyclone) and all cells were cultured in an environment at 37° C. with 5% CO2. In order to reduce interference from FBS, cells ($5 \times 10^6$) were washed twice with PBS and cultured in a serum-free medium (without FBS) for 24 hours before exosome isolation. To isolate exosomes, each supernatant obtained from the five cell lines were sequentially centrifuged at 300 g for 5 minutes, 2,500 g for 15 minutes, and 10,000 g for 30 minutes, and cells, cell debris, and microvesicles were sequentially removed. The supernatant obtained after centrifugation was filtered by a syringe filter of 0.22 μm and centrifuged at 120,000 g for 90 minutes. All processes were performed at 4° C., and the finally obtained exosomes were stored in PBS for further use.

<Example 5> Training of Deep Learning Model to Implement Classification Algorithm for Magnetic Encoded Microparticles Antibodies reacting with target exosome surface protein are conjugated to the corresponding magnetic encoded microparticles, the magnetic encoded microparticles are reacted with cell-derived exosomes, and then exposed to a rotating magnetic field, and accordingly, it was checked that different rotation patterns appeared according to each type of magnetic encoded microparticles. A convolutional LSTM deep learning model was used to decode the magnetic encoded microparticles formed horizontally, vertically, and diagonally by using a rotation video of respective magnetic encoded microparticles.

In order to train a deep learning model, a rotation pattern video of the magnetic encoded microparticles aligned in three directions (horizontal, vertical, and diagonal directions) were captured for one hour. The number of frames per second of respective images was calculated and divided into 324,000 video images, and an image having an original size of H 760×W 1200 was adjusted to a size of H 224×W 224. Images were normalized by using average and standard deviation values of all images, and 2,160 rotation images were obtained by dividing the normalized image into images in units of 5 seconds. Repeated training was conducted by using 90% of the acquired images as a training set and 10% as a test set. As a result, a model optimized by training first has accuracy of 100% in decoding the magnetic encoded microparticles. Thereafter, in order to verify performance under various conditions, multiple rotation images in units of 10 minutes were added and trained, and as a result, classification accuracy was found to be about 75%.

<Example 6> Decoding of Magnetic Encoded Microparticles Using Deep Learning

Figure 8:
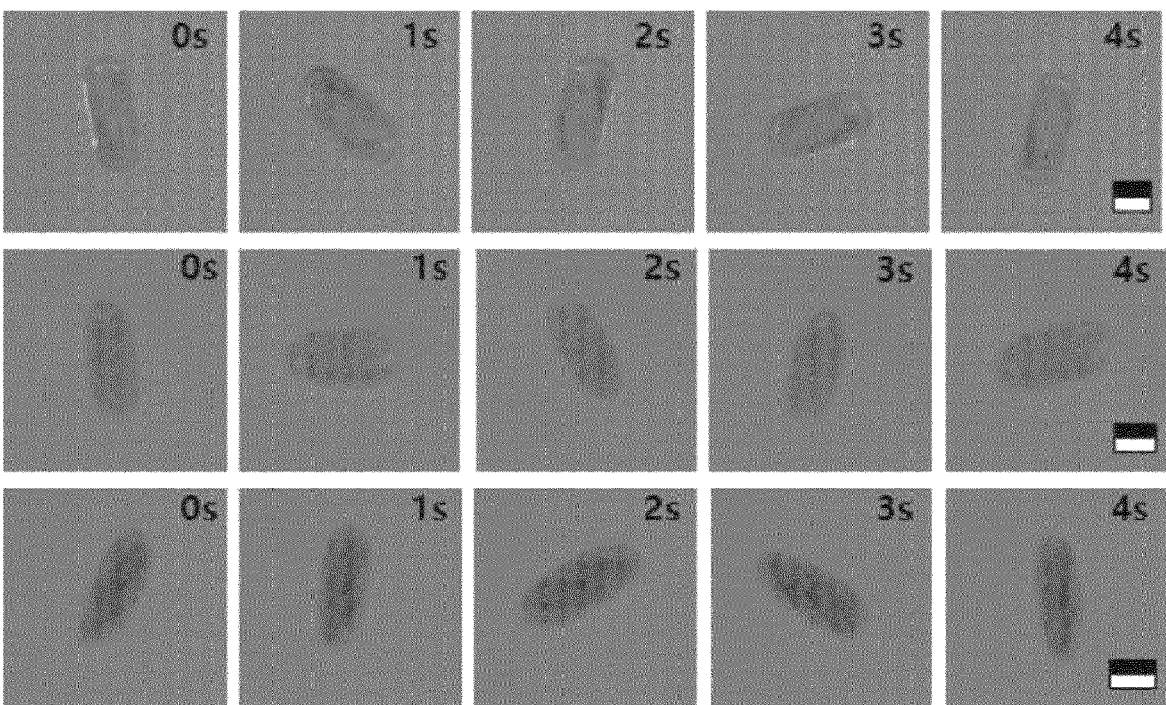
FIG. 8 illustrates images obtained by capturing magnetic encoded microparticles for each encoding type.

FIG. 8 illustrates images obtained by capturing magnetic encoded microparticles for each encoding type. FIG. 8 lists, from top to bottom, time-dependent images for magnetic encoded microparticles encoded in three directions including horizontal (0°), vertical (90°), and diagonal (45°) directions.

Magnetic encoded microparticles show specific movements depending on encoding types, that is, alignment directions. A rotation pattern appears differently depending on alignment of superparamagnetic nanoparticles (SMNPs) when the magnetic encoded microparticles are exposed to a rotating magnetic field. By using this principle, a deep learning-based classification model of the type illustrated in FIG. 6 was constructed, a rotation pattern was analyzed based on the classification model to decipher magnetic encoded microparticles (MEMPs), and multi-analysis for external protein detection was performed.

In general, an additional detection program or a complicate apparatus was required for particle decoding, but in the embodiment of the present invention, MEMP may be simply decoded without a specific device, enables multi-analysis of multiple targets at the same time, and allows fast analysis through an artificial intelligence algorithm. Also, decoding does not require multiple color labels, and accordingly, a detection process may be further simplified.

<Example 7> Exosome Detection and Quantitative Analysis Using Magnetic Encoded Microparticles A capture antibody (20 μg/ml, 80 μl in PBS) anti-PD-L1, anti-EGFR, and anti-EpCAM capable of reacting with exosome surface protein was conjugated with the magnetic encoded microparticles in horizontal (0°), diagonal (45°), and vertical (90°) directions. The magnetic encoded microparticles conjugated with each capture antibody were reacted with exosomes for 1 hour at room temperature, and then anti-CD63-biotin, anti-CD81-biotin, and anti-CD9-biotin that may react with CD63, CD81, and CD9 markers on a surface of exosome were reacted with a mixed solution prepared at a concentration of 20 μg/ml in PBS solution for 1 hour at room temperature.

FIG. 9 illustrates fluorescence intensity for each exosome concentration on magnetic encoded microparticles conjugated with different capture antibodies. FIG. 9 illustrates images of each type of magnetic encoded microparticles captured by a fluorescence microscope, and illustrates fluorescence intensity reacted on magnetic encoded microparticles in a concentration range of 0 to $4.33\times10^8$ exosomes/ml by using anti-PD-L1, anti-EGFR, and anti-EpCAM antibodies in case of MDA-MB231 cells.

Quantitative analysis of exosome surface protein was calculated by using fluorescence signal intensity of exosome marker protein, and a standard curve was obtained between fluorescence intensity and each exosome concentration. The standard curve was obtained as a relationship between fluorescence intensity and exosome concentration, and the fluorescence intensity was obtained by normalizing the fluorescence intensity value to a size of the magnetic encoded microparticle.

In addition, for multi-analysis in several cell lines, fluorescence intensity values were obtained by reacting exosomes at a specific concentration by using exosomes extracted from HEK293T, MCF7, SK-MEL-28, and HCT116 cells in the same method.

FIG. 10 illustrates diagrams of a relationship between concentration of exosomes reacted with magnetic encoded microparticles including different capture antibodies and the fluorescence intensity, according to an embodiment of the present invention. By using a standard curve, concentration values corresponding to fluorescence intensity of an image may be obtained for each type of exosome which is a target material.

<Example 8> Exosome Multi-Detection

In order to perform multi-detection, high specificity proof for a target protein is required. In order to check multi-analysis capability, three types of magnetic encoded microparticles were reacted with one biological sample to simultaneously detect exosome surface proteins PD-L1, EGFR, and EpCAM, and cross-reactivity between a specific capture antibody and non-corresponding exosome was investigated.

A protein-specific detection signal was analyzed by analyzing a rotation pattern of the magnetic encoded microparticle and measuring fluorescence intensity. As a result of comparative analysis of a case where all magnetic encoded microparticles were reacted with exosomes at once and a case where each magnetic encoded microparticle was reacted with exosome individually, it was confirmed that there was no significant difference in fluorescence intensity between the three types of magnetic encoded microparticles, and through this, it was confirmed that an all-in-one reaction could be made because there was no cross-reactivity between the exosome surface protein and each capture antibody.

<Example 9> Detection of Exosomes Derived from Four Cancer Cells

Figure 11:
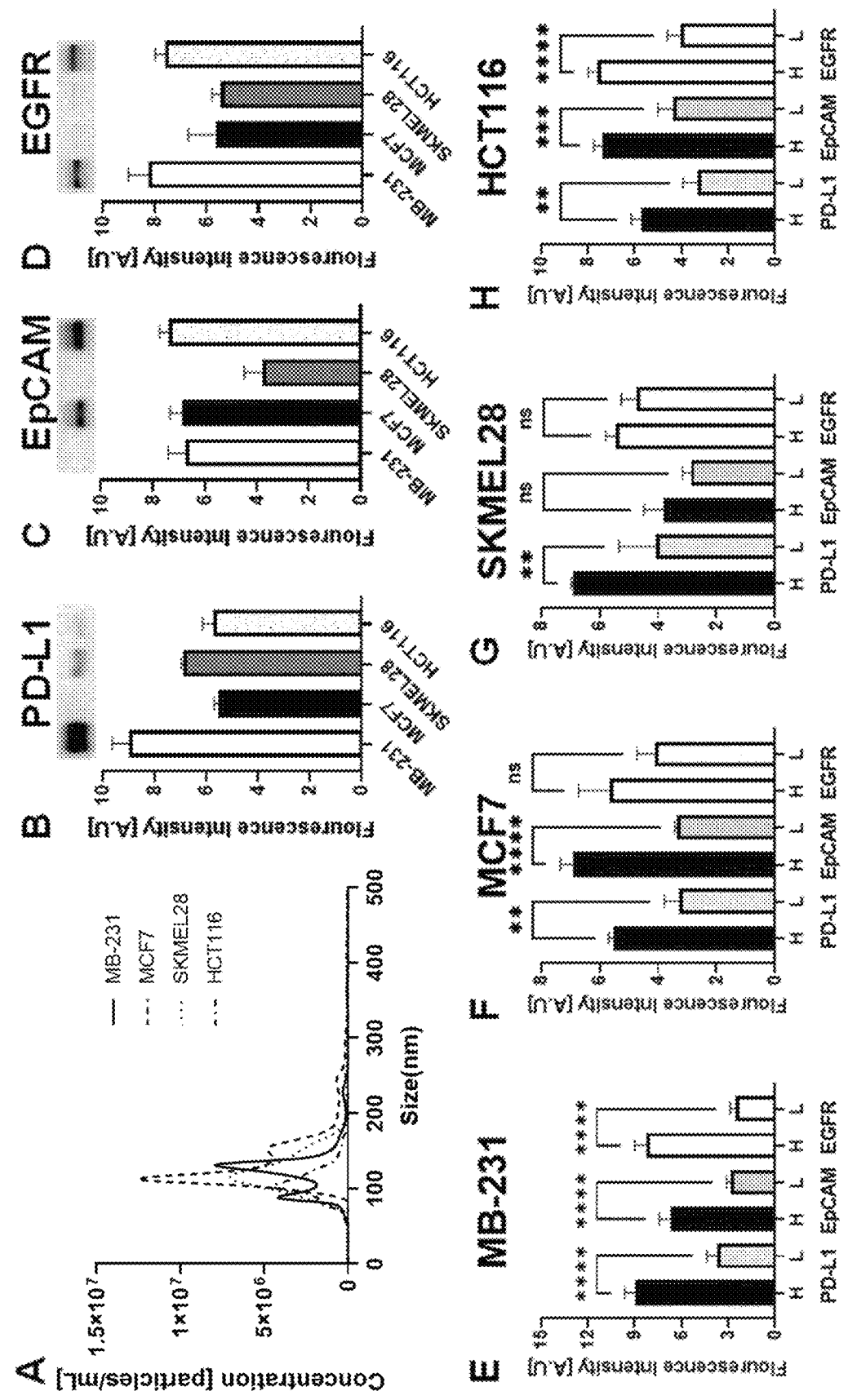
FIG. 11 illustrates diagrams of results of detecting high and low concentration exosomes derived from four types of cell lines, according to an embodiment of the present invention.

FIG. 11 illustrates diagrams of results of detecting high and low concentration exosomes derived from four types of cell lines, according to an embodiment of the present invention.

In order to check whether exosomes with different specificity may be distinguished according to respective concentrations, analysis of high and low-concentration of exosomes derived from four types of cancer cells was performed by using magnetic encoded microparticles. A of FIG. 11 illustrates concentrations of exosomes for each size derived from four types of cancer cells (MDA-MB-231, MCF7, SKMEL28, and HCT116). For an experiment, exosomes derived from MDA-MB-231, MCF7, SKMEL28, and HCT116 were classified into high-concentration exosomes 'H' and low-concentration exosomes 'L'.

First, an experiment was conducted by using high-concentration exosomes derived from MDA-MB-231, MCF7, SKMEL28, and HCT116, and the results are illustrated in B to D of FIG. 11. In this case, in order to compare expression levels of surface proteins of exosomes for each cancer cell, concentrations of exosomes derived from cancer cells used for measurement were set to substantially the same concentration (about $1\times10^8$ cells/ml).

B to D of FIG. 11 illustrate expression levels of three proteins, PD-L1, EpCAM, and EGFR, expressed on a surface of exosome for each of four types of cancer cells. In this case, Western blot results (gold standard data obtained by quantifying concentration of each protein detected from a sample) are illustrated at upper portions of graphs for comparison. As a result of comparing the fluorescence intensity according to concentration of detected exosomes with Western blot, it was able to verify that there was high similarity between the two methods (the method of the present invention and Western blot) in expression levels of PD-L1, EpCAM, and EGFR expressed on the surfaces of exosomes in each cell, and through this, performance accuracy of a detection system based on magnetic encoded microparticles developed according to the present invention was confirmed.

Next, in order to check distinguishment between concentrations of exosomes for each cancer cell, each fluorescence intensity was measured and compared by using high-concentration exosomes 'H' and low-concentration exosomes 'L' derived from MDA-MB-231, MCF7, SKMEL28, and HCT116, and the experimental results are illustrated in E to H of FIG. 11. As a result, it was confirmed through t-test that in most cases, expression levels of PD-L1, EpCAM, and EGFR on exosomes are clearly distinguished depending on exosome concentrations (low and high concentrations) of cancer cells. That is, a large difference in fluorescence intensity between low and high concentrations is observed. However, it was analyzed that there is no significant difference for each concentration in the expression level of EGFR in the MCF7 cell line and the expression levels of EpCAM and EGFR in the SKMEL28 cell line.

<Example 10> Detection of Exosomes in Clinical Patient Blood

Figure 12:
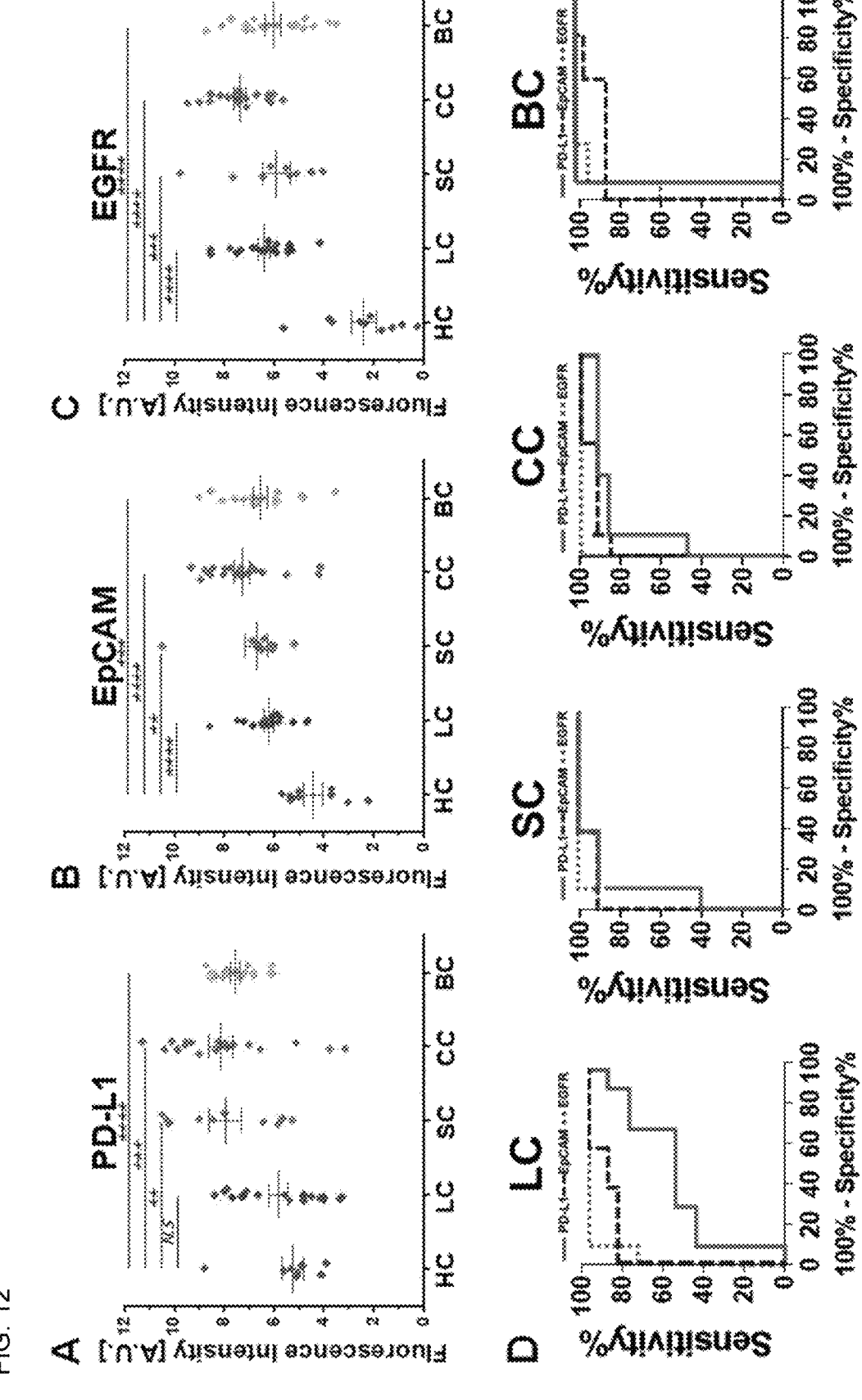
FIG. 12 illustrates diagrams of detection results of exosomes present in the blood of normal people and cancer patients (lung cancer, stomach cancer, colon cancer, and breast cancer), according to an embodiment of the present invention.

FIG. 12 illustrates diagrams of detection results of exosomes present in the blood of normal people and cancer patients (lung cancer, stomach cancer, colon cancer, and breast cancer), according to an embodiment of the present invention.

In order to test potential clinical utility of a magnetic encoded microparticle-based detection system, plasma samples of total 80 persons including 20 lung cancer patients (LC), 10 stomach cancer patients (SC), 20 colon cancer patients (CC), and 20 breast cancer patients (BC), and 10 healthy person group (HC) were used for analysis.

As a result of the analysis, as illustrated in A to C of FIG. 12, the expression levels of proteins, such as PD-L1, EpCAM, and EGFR, were found to be lower in exosomes in the plasma of a healthy person group (normal people), but the expression levels of the above proteins in exosomes of cancer patients were measured to be relatively higher. Although cancer patients and a healthy person group were successfully classified for each protein, in a case of PD-L1, it was difficult to distinguish the lung cancer patients (LC) from the healthy person group (HC). Here, the greater the number of asterisks, the better the differentiation from the healthy person group.

Also, as illustrated in D of FIG. 12, as a result of verification using a Receiver Operating Characteristics (ROC) analysis method to check detection ability of a developed detection system for each type of cancer, regarding AUC (Area Under Curve) values of lung cancer patients and a healthy person group, EpCAM and EGFR showed high detection levels of 0.920 and 0.975, but PD-L1 was calculated to be a significantly low value of 0.560. Clear differences were observed between the other cancer patients and the healthy person group.

According to the present invention described above, magnetic encoded microparticles encoded in different types are quickly and accurately identified by exposing different types of magnetic encoded microparticles to a rotating magnetic field and by performing deep learning analysis of a rotation pattern of each magnetic encoded microparticle with a video captured, and different types of target materials in a biological sample may be simultaneously detected from the video and quantitatively analyzed by using the identification result.

The present invention may identify the type of each magnetic encoded microparticle detected from a video through deep learning-based decoding, and thus, there is no need for a complex special optical apparatus to decode encrypted particles, sample analysis time may be reduced, disease-related exosomes may be quickly detected, and disease diagnosis time may be greatly shortened.

The present invention is described with reference to the embodiments illustrated in the drawings, but the embodiments are merely illustrative, and those skilled in the art to which the present invention belongs will understand that various modifications and equivalent other embodiments may be derived therefrom. Therefore, the true scope of technical protection of the present invention should be determined by the technical idea of the attached claims.

The invention claimed is:

1. A multi-detection analysis method of a biological sample, comprising:

a step of preparing a plurality of rod-shaped magnetic encoded microparticles encoded in different types, each encoding type corresponding to a different target material and each magnetic encoded microparticle being formed by aligning superparamagnetic nanoparticles in a photocurable polymer matrix in a predetermined direction under an external magnetic field and curing the polymer, wherein each magnetic encoded microparticle has a capture antibody specific to the corresponding target material attached thereto, and wherein the encoding types include a structure in which a plurality of nanoparticle blocks, each having particles aligned in a different direction, are arranged sequentially along the length of the microparticle;

a step of introducing the plurality of magnetic encoded microparticles into a sample of an analysis target and, subsequent to introducing the microparticles, introducing into the sample a detection antibody that binds to the target material and a fluorescent material that attaches to the detection antibody, thereby allowing the detection antibody to bind to the target material captured on the magnetic encoded microparticles and label the microparticles with the fluorescent material;

a step of acquiring a video of the sample in a state where the sample is exposed to a rotating magnetic field;

a step of inputting time-series images from the video into a pre-trained deep learning algorithm, the deep learning algorithm including a convolutional long-short term memory network for analyzing image and time variation information, and analyzing rotation pattern characteristics of each magnetic encoded microparticle in the video over time through the deep learning algorithm to classify each magnetic encoded microparticle; and a step of, for each classified magnetic encoded microparticle, identifying an encoding type of the microparticle based on the classification result, determining an intensity of the fluorescent material on the microparticle, and quantifying a concentration of the target material corresponding to the encoding type, thereby detecting a plurality of different target materials in the sample.

2. The multi-detection analysis method of claim 1, wherein the rotation pattern characteristics of the magnetic encoded microparticles include one or more of, a rotation speed of the magnetic encoded microparticle, a rotation cycle of the magnetic encoded microparticle; whether the magnetic encoded microparticle undergoes continuous rotation or an intermittent stop during rotation; a frequency of occurrence of an intermittent stop during rotation; and a duration of an intermittent stop.

3. A multi-detection analysis device for a biological sample, the multi-detection analysis device comprising:

one or more units being configured and executed by a processor using algorithm, the algorithm which when executed, causing the processor to perform the one or more units, the one or more units comprising:

a video acquisition unit configured to acquire an image of a sample of an analysis target while a rotating magnetic field is applied to the sample, the sample having been prepared by introducing a plurality of rod-shaped magnetic encoded microparticles encoded in different types into the sample each encoding type corresponding to a different target material and each magnetic encoded microparticle having a capture antibody specific to the corresponding target material attached thereto, and by introducing, prior to application of the rotating magnetic field, a detection antibody that binds to the target material and a fluorescent material attached to the detection antibody into the sample to react with the target material captured on the magnetic encoded microparticles such that the target material is labeled with the fluorescent material, wherein the encoding types of the magnetic encoded microparticles include a structure in which a plurality of nanoparticle blocks, each having particles aligned in different directions, are arranged sequentially along the length of the microparticle;

a decoding unit configured to input time-series images from the video into a pre-trained deep learning algorithm including a convolutional long-short term memory network, analyze rotation pattern characteristics of each magnetic encoded microparticle in the video over time via the deep learning algorithm, and classify each magnetic encoded microparticle; and a detection unit configured to, based on the classification result for each magnetic encoded microparticle, identify an encoding type of each magnetic encoded microparticle, determine an intensity of the fluorescent material attached to the detection antibody on the magnetic encoded microparticle, and quantify a concentration of the target material corresponding to the encoding type, thereby multi-detecting a plurality of types of target materials in the sample.

4. The multi-detection analysis device of claim 3, wherein the rotation pattern characteristics of the magnetic encoded microparticles include one or more of: a rotation speed of the magnetic encoded microparticle; a rotation cycle of the magnetic encoded microparticle; whether there is continuous rotation of the magnetic encoded microparticle or an intermittent stop during rotation, a frequency of occurrence of an intermittent stop during rotation; and a time length of an intermittent stop during rotation.

* * * * *